United States Patent
Burns et al.

(10) Patent No.: US 8,216,218 B2
(45) Date of Patent: Jul. 10, 2012

(54) TREATMENT APPARATUS AND METHODS FOR DELIVERING HIGH FREQUENCY ENERGY ACROSS LARGE TISSUE AREAS

(75) Inventors: Christopher J. Burns, San Jose, CA (US); Marlo Cinco, Castro Valley, CA (US)

(73) Assignee: Thermage, Inc., Hayward, CA (US)

( * ) Notice: Subject to any disclaimer, the term of this patent is extended or adjusted under 35 U.S.C. 154(b) by 1033 days.

(21) Appl. No.: 12/171,010

(22) Filed: Jul. 10, 2008

(65) Prior Publication Data

US 2009/0018628 A1 Jan. 15, 2009

Related U.S. Application Data

(60) Provisional application No. 60/948,884, filed on Jul. 10, 2007.

(51) Int. Cl.
*A61B 18/04* (2006.01)
(52) U.S. Cl. ............ 606/32; 606/41; 606/42
(58) Field of Classification Search ............ 606/32, 606/41, 42, 50; 607/99, 101, 104, 105
See application file for complete search history.

(56) References Cited

U.S. PATENT DOCUMENTS

| | | |
|---|---|---|
| 3,780,047 A | 12/1973 | Gonser |
| 4,304,235 A | 12/1981 | Kaufman |
| 4,658,819 A | 4/1987 | Harris et al. |
| 4,934,365 A | 6/1990 | Morgenthaler |
| 5,281,216 A | 1/1994 | Klicek |
| 5,487,759 A | 1/1996 | Bastyr et al. |
| 5,660,836 A | 8/1997 | Knowlton |
| 5,702,387 A | 12/1997 | Arts et al. |
| 5,718,719 A | 2/1998 | Clare et al. |
| 5,755,753 A | 5/1998 | Knowlton |
| 5,849,020 A | 12/1998 | Long et al. |
| 5,871,524 A | 2/1999 | Knowlton |

(Continued)

FOREIGN PATENT DOCUMENTS

EP 1685805 A1 8/2006

(Continued)

OTHER PUBLICATIONS

USPTO, Office Action issued in related U.S. Appl. No. 11/537,155 dated Nov. 16, 2010.

(Continued)

*Primary Examiner* — Nicholas Lucchesi
*Assistant Examiner* — Gerald Landry, II
(74) *Attorney, Agent, or Firm* — Wood, Herron & Evans, LLP (57) ABSTRACT

Apparatus and methods for treating skin conditions that deliver high frequency energy across large tissue areas. The treatment apparatus comprises a treatment tip carrying a plurality of electrodes that are switched such that fewer than all of the electrodes are concurrently energized. The treatment tip includes a cooling mechanism that cools near-surface tissue regions disposed between the skin surface and the treated tissue by cooling the respective electrode that treats each of the regions. The cooling mechanism may include a heat transfer body intervening between the electrodes and a fluid delivery member configured to discharge coolant that impinges the heat transfer body. Alternatively, the cooling mechanism may include a fluid delivery member having individually valve-controlled passages configured to discharge a dedicated stream of coolant at each of the electrodes, a thermoelectric cooler, or a closed-loop fluid delivery member.

19 Claims, 10 Drawing Sheets

U.S. PATENT DOCUMENTS

| | | | |
|---|---|---|---|
| 5,919,219 | A | 7/1999 | Knowlton |
| 5,948,011 | A | 9/1999 | Knowlton |
| 6,148,232 | A | 11/2000 | Avrahami |
| 6,241,753 | B1 | 6/2001 | Knowlton |
| 6,293,941 | B1 | 9/2001 | Strul et al. |
| 6,311,090 | B1 | 10/2001 | Knowlton |
| 6,325,799 | B1 | 12/2001 | Goble |
| 6,350,276 | B1 | 2/2002 | Knowlton |
| 6,377,854 | B1 | 4/2002 | Knowlton |
| 6,377,855 | B1 | 4/2002 | Knowlton |
| 6,381,497 | B1 | 4/2002 | Knowlton |
| 6,381,498 | B1 | 4/2002 | Knowlton |
| 6,387,380 | B1 | 5/2002 | Knowlton |
| 6,405,090 | B1 | 6/2002 | Knowlton |
| 6,413,255 | B1 | 7/2002 | Stern |
| 6,423,057 | B1 | 7/2002 | He et al. |
| 6,425,912 | B1 | 7/2002 | Knowlton |
| 6,430,446 | B1 | 8/2002 | Knowlton |
| 6,438,424 | B1 | 8/2002 | Knowlton |
| 6,453,202 | B1 | 9/2002 | Knowlton |
| 6,461,378 | B1 | 10/2002 | Knowlton |
| 6,470,216 | B1 | 10/2002 | Knowlton |
| 6,597,946 | B2 | 7/2003 | Avrahami et al. |
| 6,611,706 | B2 | 8/2003 | Avrahami et al. |
| 6,615,079 | B1 | 9/2003 | Avrahami |
| 6,696,844 | B2 | 2/2004 | Wong et al. |
| 6,708,060 | B1 | 3/2004 | Avrahami et al. |
| 6,711,435 | B2 | 3/2004 | Avrahami |
| 6,997,923 | B2 | 2/2006 | Anderson et al. |
| 7,006,874 | B2 | 2/2006 | Knowlton et al. |
| 7,022,121 | B2 | 4/2006 | Stern et al. |
| 7,062,317 | B2 | 6/2006 | Avrahami et al. |
| 7,094,215 | B2 | 8/2006 | Davison et al. |
| 7,115,123 | B2 | 10/2006 | Knowlton et al. |
| 7,123,957 | B2 | 10/2006 | Avrahami |
| 7,141,049 | B2 | 11/2006 | Stern et al. |
| 7,164,942 | B2 | 1/2007 | Avrahami et al. |
| 7,189,230 | B2 | 3/2007 | Knowlton |
| D544,955 | S | 6/2007 | Carson et al. |
| 7,229,436 | B2 | 6/2007 | Stern et al. |
| 7,257,450 | B2 | 8/2007 | Auth et al. |
| 7,267,675 | B2 | 9/2007 | Stern et al. |
| 7,276,058 | B2 | 10/2007 | Altshuler et al. |
| 7,351,252 | B2 | 4/2008 | Altshuler et al. |
| 7,422,586 | B2* | 9/2008 | Morris et al. ............ 606/41 |
| 7,452,358 | B2 | 11/2008 | Stern et al. |
| 7,473,251 | B2 | 1/2009 | Knowlton et al. |
| 7,473,252 | B2 | 1/2009 | Barry |
| 7,481,809 | B2 | 1/2009 | Stern et al. |
| 7,494,488 | B2 | 2/2009 | Weber |
| 2003/0139790 | A1* | 7/2003 | Ingle et al. ............ 607/99 |
| 2003/0163178 | A1* | 8/2003 | Davison et al. ............ 607/101 |
| 2003/0199868 | A1 | 10/2003 | Desai et al. |
| 2003/0208152 | A1 | 11/2003 | Avrahami et al. |
| 2003/0216719 | A1 | 11/2003 | Debenedictis et al. |
| 2003/0236487 | A1 | 12/2003 | Knowlton |
| 2004/0006339 | A1 | 1/2004 | Underwood et al. |
| 2004/0082940 | A1 | 4/2004 | Black et al. |
| 2004/0111087 | A1 | 6/2004 | Stern et al. |
| 2004/0116986 | A1* | 6/2004 | Cantoni et al. ............ 607/101 |
| 2004/0210214 | A1 | 10/2004 | Knowlton |
| 2005/0049582 | A1 | 3/2005 | DeBenedictis et al. |
| 2005/0171582 | A1* | 8/2005 | Matlock ............ 607/96 |
| 2005/0222555 | A1 | 10/2005 | Manstein et al. |
| 2005/0222565 | A1 | 10/2005 | Manstein |
| 2006/0004351 | A1* | 1/2006 | Arless et al. ............ 606/21 |
| 2006/0015147 | A1 | 1/2006 | Persson et al. |
| 2006/0047281 | A1 | 3/2006 | Kreindel |
| 2006/0122668 | A1 | 6/2006 | Anderson et al. |
| 2006/0206103 | A1 | 9/2006 | Altshuler et al. |
| 2007/0078454 | A1* | 4/2007 | McPherson ............ 606/41 |
| 2007/0078502 | A1 | 4/2007 | Weber et al. |
| 2007/0083247 | A1 | 4/2007 | Wyeth et al. |
| 2007/0088413 | A1* | 4/2007 | Weber et al. ............ 607/99 |
| 2007/0093797 | A1 | 4/2007 | Chan et al. |
| 2007/0093798 | A1 | 4/2007 | DeBenedictis et al. |
| 2008/0058782 | A1 | 3/2008 | Frangineas et al. |
| 2008/0082090 | A1* | 4/2008 | Manstein ............ 606/9 |
| 2009/0012434 | A1* | 1/2009 | Anderson ............ 601/6 |

FOREIGN PATENT DOCUMENTS

| | | |
|---|---|---|
| WO | 9639087 A1 | 12/1996 |
| WO | 9724073 | 7/1997 |
| WO | 9724073 A1 | 7/1997 |
| WO | 9912489 A2 | 3/1999 |
| WO | 9916502 | 4/1999 |
| WO | 0048644 A2 | 8/2000 |
| WO | 0053113 | 9/2000 |
| WO | 0100269 | 1/2001 |
| WO | 02053050 A1 | 7/2002 |
| WO | 03053266 | 3/2003 |
| WO | 03065905 A1 | 8/2003 |
| WO | 03065915 | 8/2003 |
| WO | 03065916 | 8/2003 |
| WO | 03086217 | 10/2003 |
| WO | 2004086943 | 10/2004 |
| WO | 2004087253 | 10/2004 |
| WO | 2004088700 | 10/2004 |
| WO | 2004089185 | 10/2004 |
| WO | 2004089186 | 10/2004 |
| WO | 2004089459 | 10/2004 |
| WO | 2004089460 | 10/2004 |
| WO | 2004090939 | 10/2004 |
| WO | 2004105861 | 12/2004 |
| WO | 2005096980 A1 | 4/2005 |
| WO | 2005096979 A1 | 10/2005 |
| WO | 2007030415 A2 | 3/2007 |
| WO | 2007041540 A1 | 4/2007 |
| WO | 2007046886 A1 | 4/2007 |
| WO | 2007047122 A2 | 4/2007 |
| WO | 2008091983 A2 | 7/2008 |

OTHER PUBLICATIONS

USPTO, Notice of Allowance issued in related U.S. Appl. No. 11/537,155 dated Apr. 25, 2011.

U.S. Patent and Trademark Office, Office Action issued in related U.S. Appl. No. 11/423,068.

European Patent Office, International Search Report issued in corresponding PCT Application serial No. PCT/US2008/069647 dated Oct. 6, 2008.

European Patent Office, International Search Report issued in corresponding PCT Application serial No. PCT/US2008/051868 dated Jul. 3, 2008.

European Patent Office, International Search Report issued in corresponding PCT Application serial No. PCT/US2008/051868 dated Sep. 4, 2008.

European Patent Office, International Search Report issued in corresponding PCT Application serial No. PCT/US2006/038894 dated May 31, 2007.

European Patent Office, International Search Report issued in corresponding PCT Application serial No. PCT/US2006/038536 dated Jan. 23, 2007.

European Patent Office, International Search Report issued in corresponding PCT Application serial No. PCT/US2006/022586 dated Dec. 1, 2006.

Bryan Weber et al, "Treatment Apparatus and Methods for Inducing Microburn Patterns in Tissue", U.S. Appl. No. 12/019,874, filed Jan. 25, 2008.

U.S. Patent and Trademark Office, final Office Action issued in related U.S. Appl. No. 11/423,068 dated Apr. 2, 2010.

USPTO, final Office Action issued in related U.S. Appl. No. 11/470,041 dated Dec. 8, 2011.

USPTO, Office Action issued in related U.S. Appl. No. 11/470,041 dated May 26, 2011.

USPTO, Office Action issued in related U.S. Appl. No. 12/019,874 dated Apr. 5, 2012.

* cited by examiner

TREATMENT APPARATUS AND METHODS FOR DELIVERING HIGH FREQUENCY ENERGY ACROSS LARGE TISSUE AREAS

CROSS-REFERENCE TO RELATED APPLICATIONS

This application claims the benefit of U.S. Provisional Application No. 60/948,884, filed Jul. 10, 2007, which is hereby incorporated by reference herein in its entirety.

TECHNICAL FIELD

The invention generally relates to apparatus and methods for treating tissue with high frequency energy and, more particularly, relates to apparatus and methods for delivering the high frequency energy to large areas of a patient's tissue.

BACKGROUND

Devices that can treat tissue non-invasively are extensively used to treat numerous diverse skin conditions. Among other uses, non-invasive energy delivery devices may be used to tighten loose skin to make a patient appear younger, remove skin spots or hair, or kill bacteria. Such non-invasive energy delivery devices emit electromagnetic energy in different regions of the electromagnetic spectrum for tissue treatment.

High frequency treatment devices, such as radio-frequency (RF)-based devices, may be used to treat skin tissue non-ablatively and non-invasively by passing high frequency energy through a surface of the skin to underlying tissue, while actively cooling the skin to prevent damage to a region of the tissue near the skin surface. The high frequency energy heats the tissue beneath the cooled region to a temperature sufficient to denature collagen, which causes the collagen to contract and shrink and, thereby, tighten the treated tissue. Treatment with high frequency energy also causes a mild inflammation. The inflammatory response of the treated tissue causes new collagen to be generated over time (typically, between three days and six months following treatment), which results in further tissue contraction.

Modern high frequency treatment devices employ a high frequency generator and treatment tips having electrodes coupled with the high frequency generator. Conventional electrodes consist of a pattern of metallic features carried on a flexible electrically insulating substrate, such as a thin film of polyimide. The temperature of the treatment tip is measured by temperature sensors, such as thermistors or thermocouples, carried on the treatment tip.

Among other purposes, the output of the temperature sensors is used for closed-loop control of coolant application and/or detecting aberrant skin temperatures as a safety precaution. Specifically, the non-patient side of the electrode in the treatment tip may be sprayed with a coolant or cryogen spray under feedback control of the temperature sensors for cooling the tissue region proximate to the skin surface. The controller triggers the coolant spray based upon an evaluation of the temperature readings from the temperature sensors.

Treatment tips exhibit dimensional restrictions established by power constraints of the high frequency generator. Consequently, the surface area of the electrode carried by the treatment tip is constrained at least in part by the electrical load imposed on the high frequency generator. This size restriction on the electrode limits the rate or speed by which the treatment tip can be used to conduct a procedure on a patient.

What is needed, therefore, are apparatus and methods for treating skin conditions that deliver high frequency energy over a larger surface area than possible using conventional treatment tips, as well as overcoming other deficiencies of conventional treatment tips.

SUMMARY

The invention is generally directed to treatment apparatus and methods that deliver high frequency energy to tissue underlying a skin surface across a larger surface area during non-invasive tissue treatments. The treatment apparatus generally includes a plurality of electrically-isolated electrodes each configured to deliver the high frequency energy to a respective one of a plurality of regions of the tissue. Preferably, the electrodes deliver energy sequentially either individually or in selected groups to the patient's tissue.

In one embodiment, the treatment apparatus may include a heat transfer member which acts as a heat sink and which contacts the electrodes. The heat transfer member contacts the electrodes in a relationship that promotes heat transfer between the electrodes and the heat transfer member. In one embodiment, the heat transfer member is positioned to receive the coolant discharged from the fluid delivery member. Alternatively, the heat transfer member can be cooled by a thermoelectric cooler or cooled using a closed loop water or other fluid cooling circuit. In yet a further embodiment, closed loop water or other fluid cooling circuit can be used to directly cool a back surface of the electrodes without any intervening heat transfer member.

In another embodiment, the apparatus may further include a high frequency power supply electrically coupled in a circuit with the electrodes. The radiofrequency energy source is adapted to energize the electrodes to deliver the high frequency energy to the tissue. A switching element is disposed in the circuit. The switching element is adapted to open and close a current path in the circuit to each of the electrodes so that each of the electrodes can be individually activated for delivering the high frequency energy to a respective one of the regions of the tissue.

In another embodiment, the tissue treatment method includes cooling a first electrode from among multiple electrodes with coolant to cool a first region of the tissue proximate to the first electrode. The electrodes are electrically isolated from each other. The method further includes delivering high frequency energy from the first electrode, while cooled, over a first time period to treat the cooled first region of the tissue. The method further includes cooling a second electrode with coolant during the first time period to cool a second region of the tissue.

In another embodiment, a method of operating a tissue treatment apparatus is provided for treating tissue located beneath a skin surface with high frequency energy from a plurality of electrodes that are electrically isolated from each other. The method comprises delivering the high frequency energy from the first electrode over a first time period to treat a first region of the tissue and, after the conclusion of the first time period, delivering the high frequency energy from the second electrode over a second time period to treat a second region of the tissue.

BRIEF DESCRIPTION OF THE DRAWINGS

The accompanying drawings, which are incorporated in and constitute a part of this specification, illustrate embodiments of the invention and, together with a general descrip

DETAILED DESCRIPTION

Figure 1:
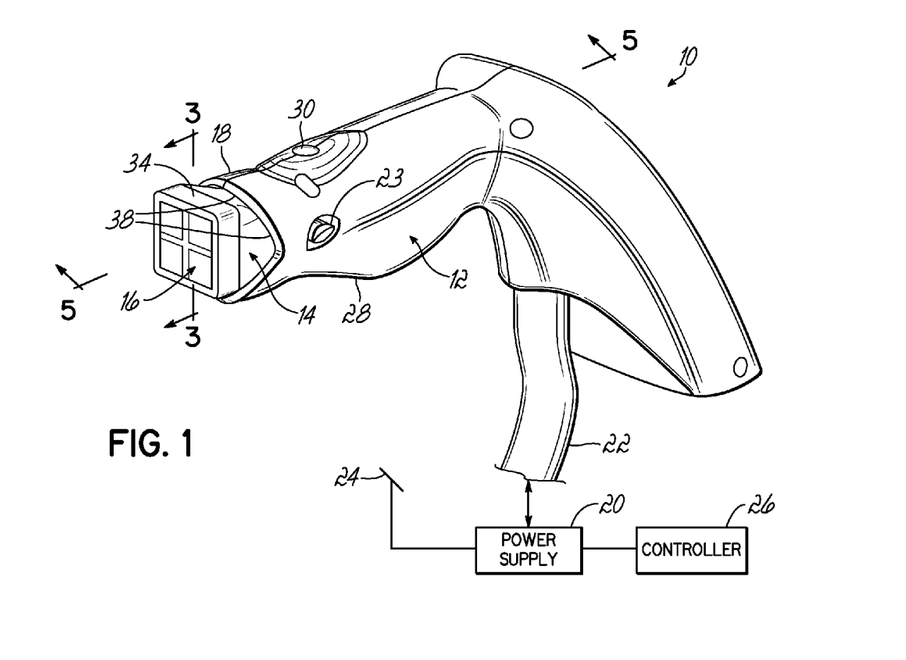
- FIG. 1 is a perspective view of a handpiece and a treatment tip in accordance with an embodiment of the invention coupled with the handpiece.
Figure 5:
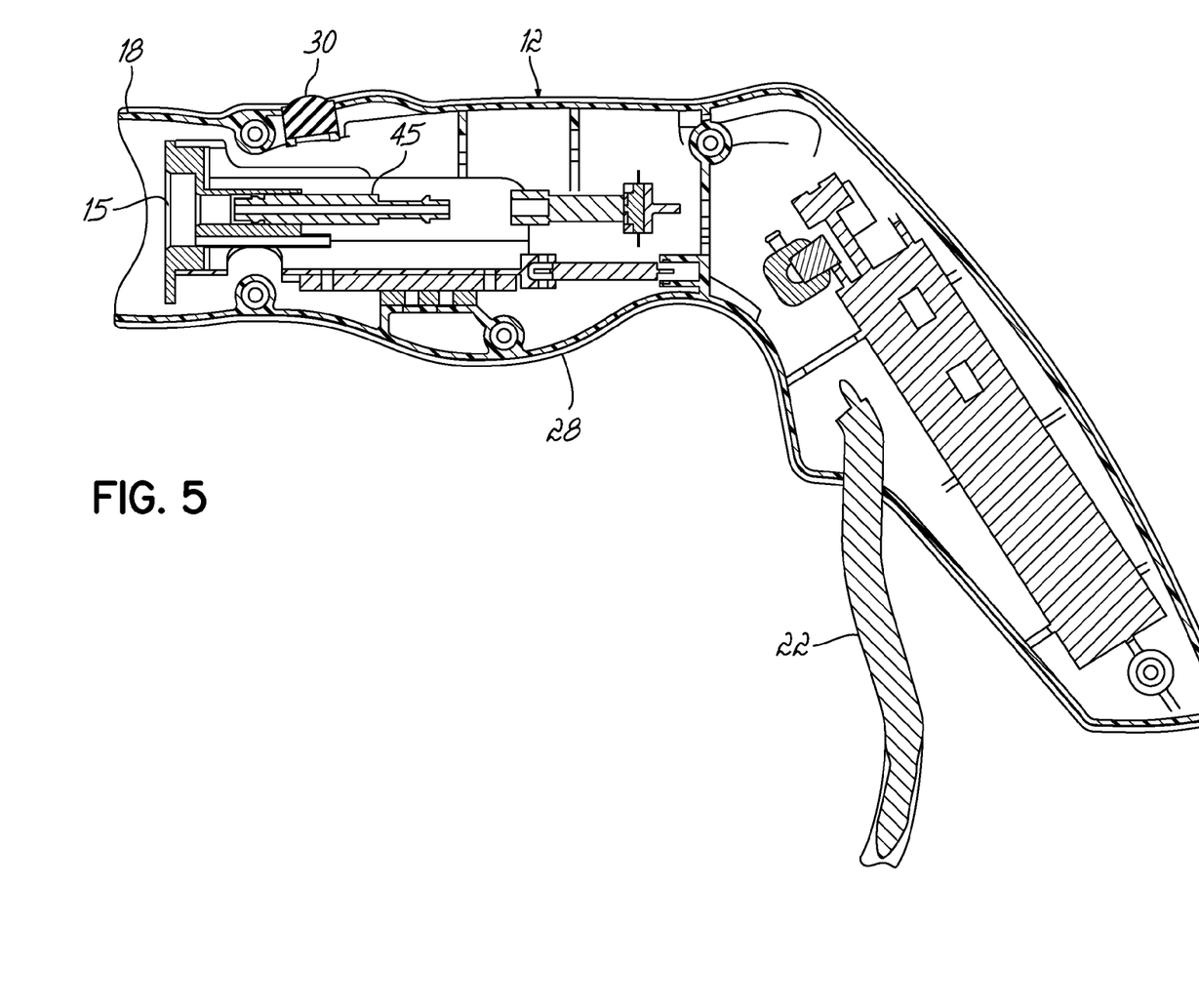
FIG. 5 is a cross-sectional view taken generally along line 5-5 in FIG. 1 with the treatment tip removed for clarity.

With reference to FIG. 1, a treatment apparatus 10 includes a handpiece 12, a treatment tip 14 releasably coupled with the handpiece 12, and an energy delivery member 16 carried by the treatment tip 14. The handpiece 12 is typically composed of a plastic or polymer material, such as a cured polymer resin, that is molded, such as by an injection molding process, into a three-dimensional shape. Defined at a distal end of the handpiece 12 is a shroud 18 that surrounds the entrance to a mounting socket 15 (FIG. 5) that is dimensioned and shaped to receive the treatment tip 14. Disposed inside the mounting socket 15 are couplings used for establishing electrical and fluid connections with the treatment tip 14. The handpiece 12 and treatment tip 14 are joined together in a suitable manner that will house the mechanical and electrical connections described herein or otherwise used to create a functional treatment apparatus 10.

The energy delivery member 16 is electrically coupled with a high frequency power supply 20 that includes an electrical circuit (not shown) operative to generate electrical energy in the form of high frequency electrical current. A typical operating frequency for the high frequency power supply 20 is in the radio-frequency (RF) region of the electromagnetic spectrum. The operating frequency of power supply 20 may advantageously be in the range of several hundred KHz to about 60 MHz to impart a therapeutic effect to treat target tissue beneath a patient's skin surface. In one specific embodiment, the operating frequency of power supply 20 may be about six (6) MHz, although the invention is not so limited.

The circuit in the power supply 20 converts a line voltage into drive signals having an energy content and a duty cycle appropriate for the amount of power and the mode of operation that have been selected by the clinician, as understood by a person having ordinary skill in the art. A connecting cable 22 extends exteriorly of a proximal end of the handpiece 12 for establishing an electrically coupled relationship with the high frequency power supply 20 in order to define a current path for high frequency electrical current supplied to energy delivery member 16 in the treatment tip 14. Conductors or wires (not shown) inside the handpiece 12, which may be insulated and shielded, transfer the high frequency electrical current from the connecting cable 22 to the energy delivery member 16.

A non-therapeutic passive or return electrode 24 (FIG. 1) is electrically coupled with a negative voltage polarity terminal of the high frequency power supply 20. The return electrode 24 is physically attached to a body surface of the patient (i.e., the patient's lower back). During treatment, high frequency current flows through the bulk of the patient between the energy delivery member 16 and the return electrode 24 in a closed circuit or RF current path. Current delivered by the energy delivery member 16 is returned to the high frequency power supply 20 from the return electrode 24, after having been conducted through the tissue of the patient and heating the treated tissue regions, to define a closed circuit. Because of the low current density delivered across the relatively large surface area of the return electrode 24 in contact with the patient, the return electrode 24 is non-therapeutic in that no significant heating is produced in tissue adjacent to its attachment site to the patient's body. High frequency electrical current flowing between the energy delivery member 16 and the patient is at its highest density at the skin surface and tissue adjacent to the energy delivery member 16 and, therefore, delivers a therapeutic effect to these tissue regions.

A controller 26 regulates the power delivered from the high frequency power supply 20 to the energy delivery member 16 by controlling and supervising the operational parameters of the high frequency power supply 20. The controller 26 may include user input devices to, for example, adjust the energy amplitude level of high frequency power supply 20 or switch between different modes of operation. The controller 26 includes a processor, which may be any suitable conventional microprocessor, microcontroller or digital signal processor, executing software to implement control algorithms for the high frequency power supply 20. Controller 26 may also include a nonvolatile memory (not shown) containing programmed instructions for the processor and, in addition, may be optionally integrated into the power supply 20. Controller 26 may also communicate, for example, with a nonvolatile memory carried by the handpiece 12 or the treatment tip 14.

Handpiece 12, which is hand held, includes a smoothly contoured grip portion 28 having a shape suitable for gripping and handling by a clinician. The grip portion 28 is adapted to be grasped by at least one hand of the clinician for manipulating the handpiece 12 to maneuver the treatment tip 14 and energy delivery member 16 to a location proximate to the skin surface and, typically, in a contacting relationship with the skin surface. Representative handpieces 12 suitable for use in the invention are shown and described in commonly-assigned U.S. Pat. Nos. 7,115,123 and 7,141,049; the disclosure of each of which is hereby incorporated by reference herein in its entirety.

An activation button 30, which is accessible to the clinician from the exterior of the handpiece 12, is depressed and released for actuating a switch that selectively couples the energy delivery member 16 with the high frequency power supply 20. In this manner, the activation button 30 controls the delivery of high frequency energy from the energy delivery member 16 to treat the tissue. The treated tissue regions receiving the therapeutic effect may be the epidermis, the dermis, or other subcutaneous tissue types. High frequency energy is delivered from energy delivery member 16 to the patient's skin surface and the underlying tissue regions over a short delivery cycle as the individual electrodes 60, 62, 64, 66 (FIGS. 4, 4A) are sequentially energized. After the activation button 30 is released, the handpiece 12 is manipulated by the clinician to position the treatment tip 14 near a different region of the skin surface for another treatment cycle of high frequency energy delivery to the patient's tissue.

With reference to FIGS. 1, 2, 2A, 3, and 5, according to one embodiment of the invention, the treatment tip 14 includes an outer shell 34 defining an enclosure or housing, a fluid delivery member 36 stationed inside the housing, and a heat transfer body 35. The heat transfer body 35, which may have a construction characteristic of a heat spreader and heat sink, is disposed between the fluid delivery member 36 and the energy delivery member 16. The outer shell 34 includes slots 25 used in coupling the treatment tip 14 with the handpiece 12. The handpiece 12 includes spring-loaded buttons 23 that engage the slots 25 when the handpiece 12 and treatment tip 14 are coupled together.

The outer shell 34 is a tubular member that includes a tubular section 27, a tubular section 29 of greater cross-section area than section 27, and a flared tubular section 31 smoothly joining the sections 27, 29 of different cross-sectional area. A wall 33 is defined generally at the intersection between the tubular sections 27 and 31 of outer shell 34. A flange 37 projecting outwardly from one end of the fluid delivery member 36 has a contacting or near-contacting relationship with the wall 33 when the treatment tip 14 is assembled.

The fluid delivery member 36 includes a fluid coupling members 40, 42 that cooperate to deliver coolant to the heat transfer body 35. In an assembled condition, the fluid coupling members 40, 42 of fluid delivery member 36 are nested together with the heat transfer body 35 inside the housing defined by the outer shell 34. The energy delivery member 16 is exposed through a window 38 defined about the open end of the tubular section 29 of outer shell 32.

Fluid coupling member 42 includes a conduit 43 that extends rearwardly through a passageway 44 defined in the wall 33 of outer shell 34. The conduit 43 defines a lumen for a fluid path that conveys a flow of coolant to the fluid coupling member 40. The fluid coupling member 40 includes a plurality of passages 48 oriented to deliver a spray or stream of a cryogen or coolant toward the heat transfer body 35 for controlling the temperature of the energy delivery member 16 and the patient's epidermis.

The coolant is pumped from a coolant supply (not shown) to a valve member 45 (FIG. 5) that is mechanically coupled with a fitting 39 (FIG. 3) formed radially inside section 27 of the outer shell 34. The fitting 39 is accessible inside of a cylindrical shield 61 projecting rearwardly from wall 33. The valve member 45 is hydraulically coupled with the lumen of the conduit 43. The valve member 45 may precisely meter the flow of coolant to the fluid delivery member 36. Operation of the valve member 45 may be controlled by controllers in either, or both, of the power supply 20 and the handpiece 12.

The cylindrical shield 61 is located radially between the fitting 39 and the tubular section 27.

The fluid coupling member 42 further includes a housing 46, a central cavity 49 defined in the housing, and a plurality of channels 50 defined in the housing 46 that extend radially outwardly from the central cavity 49. The central cavity 49 communicating with an outlet 41 of the conduit 43 of fluid coupling member 42. The channels 50 may be arranged circumferentially about the perimeter of the central cavity 49 at approximately equal angular increments. Each of the channels 50 extends an open end communicating with the central cavity 49 to a closed end 47 remote from the open end. The closed end 47, which may be curved, is located proximate to an inlet of the passage 48 in a respective one of the passages 48. A flow of coolant is communicated along each of the channels 50 from the central cavity 49 to the corresponding closed end 47 and then to a respective one of the passages 48.

The fluid coupling member 40 includes a housing 39 and a set of raised arms 53 defined in the housing 39 that are complementary in shape and dimensions to the channels 50 of the fluid coupling member 42. The raised arms 53 fan radially outwardly from a central raised region 58 and, in the assembled treatment tip 14, face toward the fluid coupling member 42. Each of the raised arms 53 is received in a respective one of the channels 50 of fluid coupling member 42 and the central raised region 58 is received in the central cavity 49 of fluid coupling member 42. Coolant flows in an open space 57 (FIG. 3) that is defined between the central cavity 49 and central raised region 58 and between the arms 53 and channels 50 to the inlets of the passages 48.

The heat transfer body 35, which promotes improved thermal management of the energy delivery member 16, includes a base 51 having a rear surface 54 facing the passages 48 of the fluid coupling member 40 and a front surface 56. When the treatment tip 14 is assembled, the front surface 56 of the base 51 faces a rear surface of the energy delivery member 16 and the rear surface 54 of the heat transfer body 35 is exposed to the coolant discharged from passages 48. In addition, the perimeter of the heat transfer body 35 abuts against a shoulder 59 (FIG. 3) extending about the fluid coupling member 42.

A set of substantially parallel fins 55 projects from the rear surface 54 of the base 51. The fins 55 are defined by a set of substantially parallel grooves 52 in which adjacent fins 55 are separated by one of the grooves 52. The grooves 52 and fins 55 operate to increase the effective surface area of the heat transfer body 35 that is available for cooling by the presence of the coolant. The groove width is selected such that coolant can readily penetrate into the grooves 52 and wet substantially the entire rear surface 54. The base 51 is disposed between the fins 55 and the energy delivery member 16.

The fluid coupling member 40, heat transfer body 35, and the forward end of the fluid coupling member 42 are located radially inside of section 29 of the outer shell 34. The forward end of the fluid coupling member 42 is disposed between section 29 and the fluid coupling member 40 and between section 29 and the heat transfer body 35. The forward end of the fluid coupling member 42 and the front surface 56 of the heat transfer body 35 project a short distance beyond the outer shell 34. The front surface 56 of the heat transfer body 35 projects a short distance beyond the forward end of the fluid coupling member 42. When the treatment tip 14 is mechanically coupled with the handpiece 12 to form the functional treatment apparatus 10, the front surface 56 of the heat transfer body 35 protrudes beyond the shroud 18 of the handpiece 12 so that the energy delivery member 16 is exposed and visible.

Heat energy originating from the patient's tissue, when the energy delivery member 16 is powered, in contact with the skin surface, and operating to treat tissue beneath the skin surface, is transferred in a thermal conduction path extending through the energy delivery member 16 and then from the front surface 56 of the heat transfer body 35 through its thickness to the rear surface 54. The transferred heat energy, which is withdrawn from the patient's tissue, is dissipated by the coolant directed onto the rear surface 54 of the heat transfer body 35. For example, the transferred heat energy may be dissipated by evaporation of the sprayed coolant. The heat transfer may operate to cool the tissue contacted by the energy delivery member 16 so that the depth of tissue treatment does not intersect the skin surface.

As the height of the fins 55 or, equivalently, the depth of the grooves 52 is increased, the effective surface area of the heat transfer body 35 contacted by the coolant increases. This may increase the effectiveness of the heat transfer body 35 as a heat sink for the patient's tissue. Although the fins 55 are depicted as having planar sidewalls, the fins 55 may have any appropriate type or geometry, such as posts or pins, angled sidewalls, or any other fin construction familiar to a person having ordinary skill in the art.

The heat transfer body 35 is formed of a thermally conductive and electrically insulating dielectric material, in which the thermal conductivity is selected based upon the heat transport relationship to be maintained. One suitable dielectric material is boron nitride. In certain embodiments, the material forming the heat transfer body 35 may have a thermal conductivity at 212° F. greater than about 100 (Btu/hr·in/ft$^2$) and an electrical resistivity greater than about $10^8$ Ω-cm.

Figure 4:
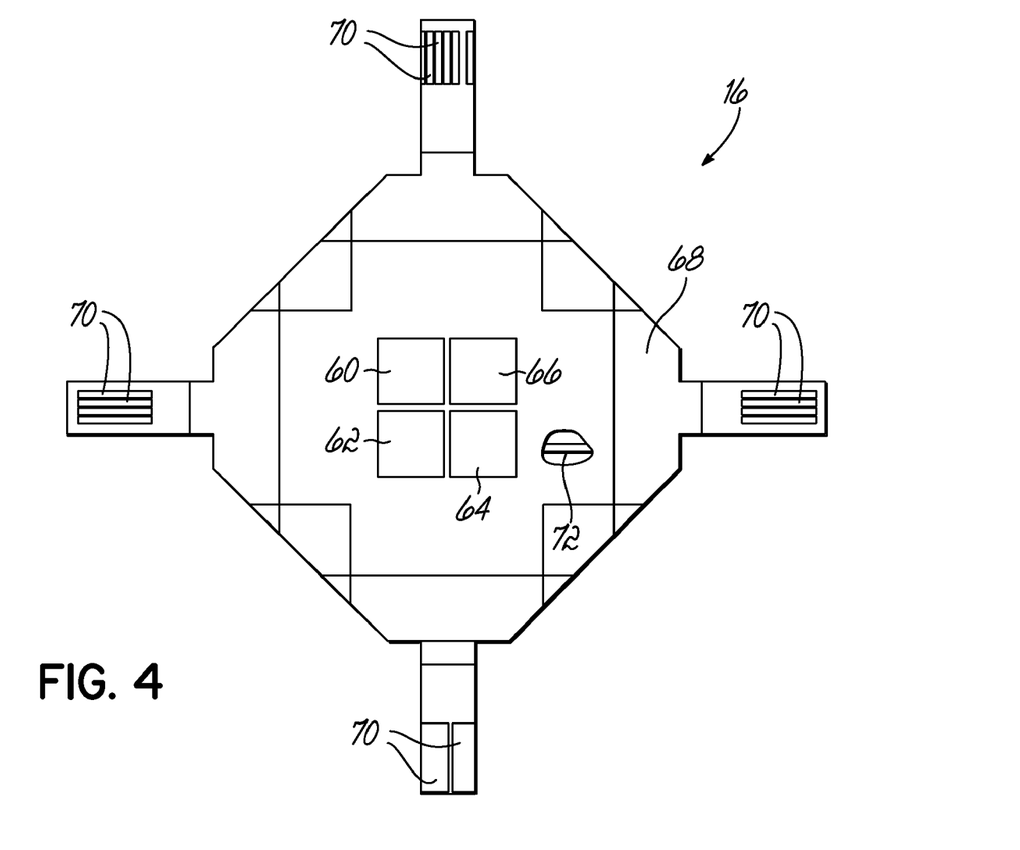
FIG. 4 is a front view of an energy delivery member for use with the treatment tip of FIGS. 2, 2A, and 3.
Figure 4A:
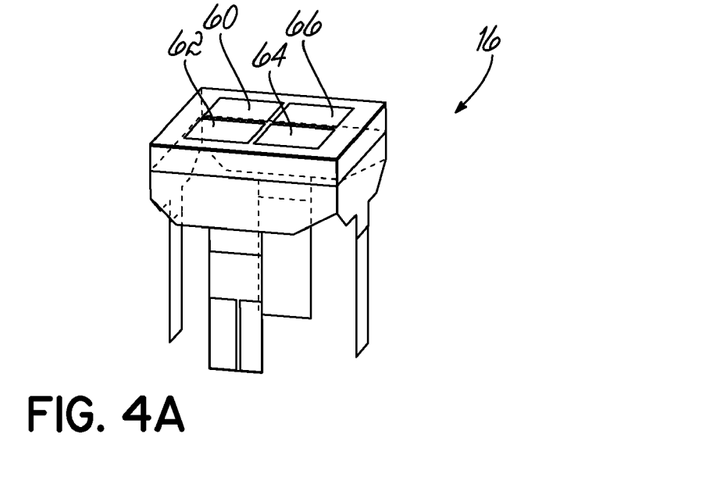
FIG. 4A is a perspective view of the energy delivery member folded about the portion of the treatment tip shown in FIG. 3.

With reference to FIGS. 4 and 4A, the individual electrodes 60, 62, 64, 66 of the energy delivery member 16 comprise conductive features supported by an insulating substrate 68, which in the representative embodiment of the invention is a flexible sheet of dielectric material. The insulating substrate 68 may comprise a thin flexible base polymer (e.g., polyimide) film carrying thin conductive (e.g., copper) traces or leads 72 electrically coupling the electrodes 60, 62, 64, 66 with contact pads 70. The energy delivery member 16 may comprise a flex circuit having a patterned conductive (i.e., copper) foil laminated to a base polymer (or other non-conductive material) film or patterned conductive (i.e., copper) metallization layers directly deposited on a base polymer film by, for example, a vacuum deposition technique, such as sputter deposition. Flex circuits, which are commonly used for flexible and high-density electronic interconnection applications, have a construction understood by a person having ordinary skill in the art. The insulating substrate 68 is arranged or disposed between the electrodes 60, 62, 64, 66 and the tissue such that, during a non-invasive tissue treatment, the energy is transmitted from the electrodes 60, 62, 64, 66 through the insulating substrate 68 by capacitively coupling with the tissue.

The insulating substrate 68 of the energy delivery member 16 is wrapped or folded about the heat transfer body 35 and fluid delivery member 36, as best shown in FIG. 4A and as understood by a person having ordinary skill in the art. In the folded state in the assembled treatment tip 14, the contact pads 70 of the energy delivery member 16 are exposed through slots 74 extending through the wall 33 of the outer shell 34. The mounting socket 15 (FIG. 5) in the handpiece 12 includes electrical contacts (not shown), such as pogo pin contacts, used to establish electrical continuity with the contact pads 70. The contact pads 70 may also be used to couple other structures (not shown), such as temperature sensors, impedance sensors, or pressure sensors, with controller 26 or another controller (not shown) either inside the handpiece 12 or external to the handpiece 12.

The portion of the insulating substrate 68 carrying electrodes 60, 62, 64, 66 has a contacting relationship with the front surface 56 of the heat transfer body 35 that promotes heat transfer across the interface of contact. The electrodes 60, 62, 64, 66 are positioned such that one of the electrodes 60, 62, 64, 66 is disposed in each of the four quadrants of the front surface 56. The electrodes 60, 62, 64, 66, which are electrically isolated from each other, may have identical surface areas or different surface areas. In one embodiment, each of the individual electrodes 60, 62, 64, 66 has a surface area of about three mm$^2$.

Figure 4B:
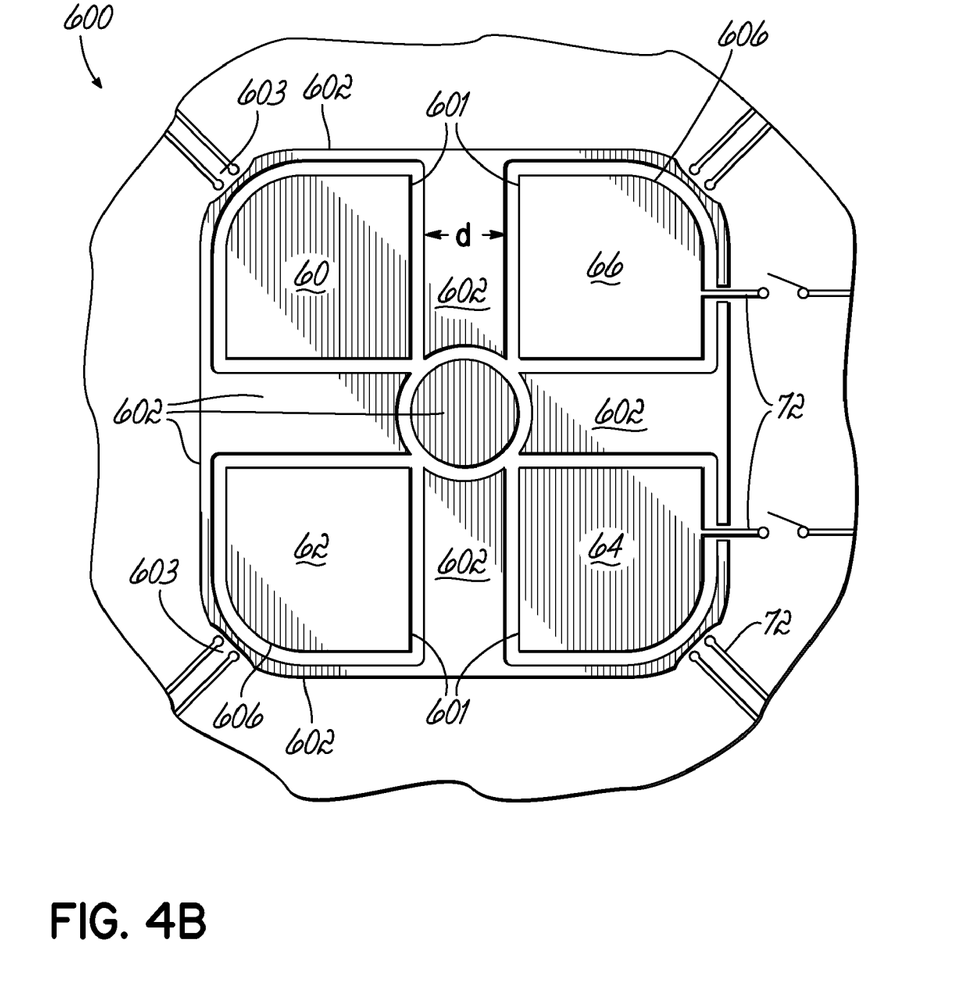
FIG. 4B is a front view of an alternative embodiment of an electrode structure for use with the treatment tip of FIGS. 2, 2A, and 3.

Referring to FIG. 4B, an alternative embodiment of a portion of an electrode structure for use in an energy delivery member 600, which is otherwise similar to energy delivery member 16, is shown. In this embodiment, inside edges 601 of the electrodes 60, 62, 64, 66 are separated from each another by a small but significant distance, d. If the distance, d, is minimal, tissue beneath each of the inside edges 601 can be over-heated because this tissue will be heated each time one of the electrodes 60, 62, 64, 66 adjacent to it is energized. In other words, tissue between the electrodes 60, 62 in FIG. 4B is heated first when electrode 60 is energized, then again when electrode 62 is energized, so this tissue would be hotter than tissue beneath a middle of the electrodes 60, 62, and result in uneven tissue heating. To minimize this effect, the distance, d, is specified as shown in FIG. 4B so that "hot" spots between electrodes 60, 62, 64, 66 do not occur or are minimized, and tissue between the middle of the electrodes is heated by roughly the same amount as tissue between the electrode edges 601.

To facilitate heat transfer from tissue between the electrodes 60, 62, 64, 66 and tissue adjacent outside edges 606 of the electrodes 60, 62, 64, 66, electrically isolated and thermally conductive metal sections 602 are provided near the outside edges 606. Electrically isolating the metal sections 602 minimizes cross talk between electrodes 60, 62, 64, 66 as they are individually energized. The metal sections 602 insure tissue therebeneath is adequately cooled by the heat transfer body 35. Without the isolated metal sections 602, a thermally insulative air gap would exist between tissue and the heat transfer body 35. Also shown are four thermistors 603 for measuring temperature at the four corners of the electrode structure.

Figure 6:
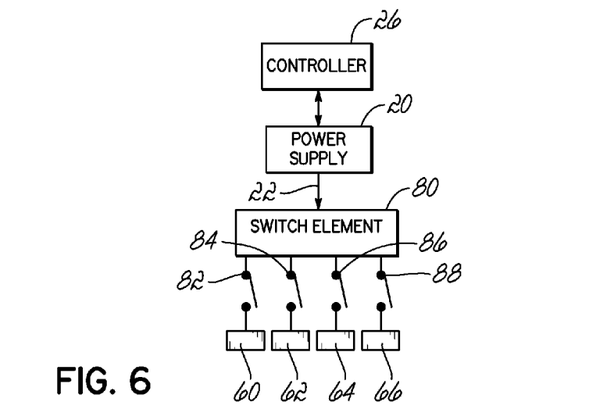
FIG. 6 is a diagrammatic view of a circuit diagram showing the electrical connections between the electrodes of the energy delivery member and the power supply.

With reference to FIG. 6, the electrodes 60, 62, 64, 66 of either FIGS. 4, 4A or FIG. 4B are electrically coupled in parallel with the high frequency power supply 20 through a switching element 80 that can select which of the electrodes 60, 62, 64, 66 is electrically coupled with the power supply 20 at any instant in time. To that end, the switching element 80 includes switches 82, 84, 86, 88, such as relays or another type of switching device or circuit, that are adapted to be switched between closed and open conditions. In the closed condition, a signal or current path is established that electrically connects one of the terminals of the high frequency power supply 20 and a respective one of the electrodes 60, 62, 64, 66. In the open condition, the respective one of the electrodes 60, 62, 64, 66 is disconnected from the high frequency power supply 20. The switching element 80 may be integrated into the controller 26, integrated into the power supply 20, integrated into the treatment tip 14, or may constitute a separate circuit element controlled by either the controller 26 or power supply 20. The switching element 80 permits the electrodes 60, 62, 64, 66 to be individually energized in the closed circuit with the power supply 20.

In use and with reference to FIGS. 1-5, the metered coolant spray is directed from the passages 48 in the fluid coupling member 40 to the heat transfer body 35. The cooled heat transfer body 35 operates as a heat sink for pre-cooling the patient's tissue adjacent to the electrodes 60, 62, 64, 66 by heat transfer through the energy delivery member 16 of treatment tip 14. After a short interval to permit the tissue to be cool to a targeted pre-cool temperature, switch 82 of switching element 80 is actuated to close the current path between electrode 60 of the energy delivery member 16 and power supply 20. The other switches 84, 86, 88 remain in an open condition so that the circuit is open to electrodes 62, 64, 66. Actuating switch 82 causes the electrode 60 to be energized by the high frequency power supply 20 to deliver high frequency energy over a first time period to treat the first region of the tissue beneath the electrode 60 and around its edges 601, 606 (FIG. 5A). If needed, additional amounts of coolant may be delivered from the fluid coupling member 40 to the heat transfer body 35 to maintain a suitable cooling profile for removing heat from the patient's tissue during energization of any or all of the electrodes 60, 62, 64, 66.

The pre-cooling of the tissue proximate to the electrodes 60, 62, 64, 66 prohibits the high frequency energy delivered to the tissue from heating regions of the tissue proximate to the skin surface to a temperature sufficient to cause significant thermal damage or other undesired thermal effects. Depths of tissue in these regions that are not significantly cooled by pre-cooling will warm up to therapeutic temperatures, which produces the desired therapeutic effect. The amount or duration of pre-cooling may be used to select the protected depth of untreated tissue in each region. Longer durations of pre-cooling produce a deeper protected zone in the tissue. The converse is true for briefer periods of pre-cooling.

At the conclusion of the first time period, switch 82 of switching element 80 is opened to open the current path from the power supply 20 to electrode 60. A second tissue region proximate to electrode 62 is then treated with high frequency energy by actuating switch 84 to a closed position to close the circuit with the power supply 20. Switches 82, 86 and 88 of the switching element 80 remain open. Because the second tissue region has already been precooled, high frequency energy may be delivered to the second tissue region over a second time period with a minimal time delay after the first time period. While the second tissue region is being treated over the second time period, the first region receives a post-cooling treatment. A third tissue region proximate to electrode 64 is pre-cooled in anticipation of subsequent treatment with high frequency energy at the conclusion of the second time period. In a similar manner, the switching element 80 is used to serially close the current path between a respective one of the electrodes 64, 66 of the energy delivery member 16 and the power supply 20 to treat the third tissue region and a fourth tissue region proximate to electrode 66. During this process, all electrodes can be cooled equally, or alternatively coolant can be delivered through specific passages as shown in FIG. 9A to cool successive electrodes or combinations thereof sequentially.

As a result of the switching on and off of the electrodes, the electrodes 60, 62, 64, 66 are sequentially energized by power supply 20 to deliver high frequency energy to different regions of the patient's tissue beneath the skin surface while the energy delivery member 16 is proximate but external to the skin surface. Only one of the electrodes 60, 62, 64, 66 is energized with high frequency energy at any instant in time, though the invention also includes the concept that multiple electrodes or groups of electrodes be energized at any one time. After all electrodes 60, 62, 64, 66 are energized, the treatment tip 14 is re-located to a different treatment site and the process is repeated.

Because of the switching, high frequency energy can be delivered across the individual surface area of each of the electrodes 60, 62, 64, 66 with a single pre-cooling event and without moving the treatment tip 14. However, the load on the power supply 20 is limited as only one of the electrodes 60, 62, 64, 66 (or any one group of these electrodes) is energized at any one time during the treatment. Scaling the surface area of the individual electrodes 60, 62, 64, 66 changes the treatment area for the tissue region at each treatment site.

The coolant directed from the fluid coupling member 40 to the heat transfer body 35 may also be used to cool portions of the tissue regions after heating by the transferred high frequency energy from electrodes 60, 62, 64, 66. Post-cooling may prevent or reduce heat delivered deeper into the tissue from conducting upward and heating shallower tissue regions, such as the epidermis, to temperatures which could burn the epidermis even though external energy delivery to the targeted tissue has ceased. Optionally, the coolant spray may be supplied during high frequency energy delivery to the tissue at the treatment site. Suitable coolants for the coolant spray include, but are not limited to, R134a refrigerant, nitrogen, and R152a refrigerant.

Figure 7:
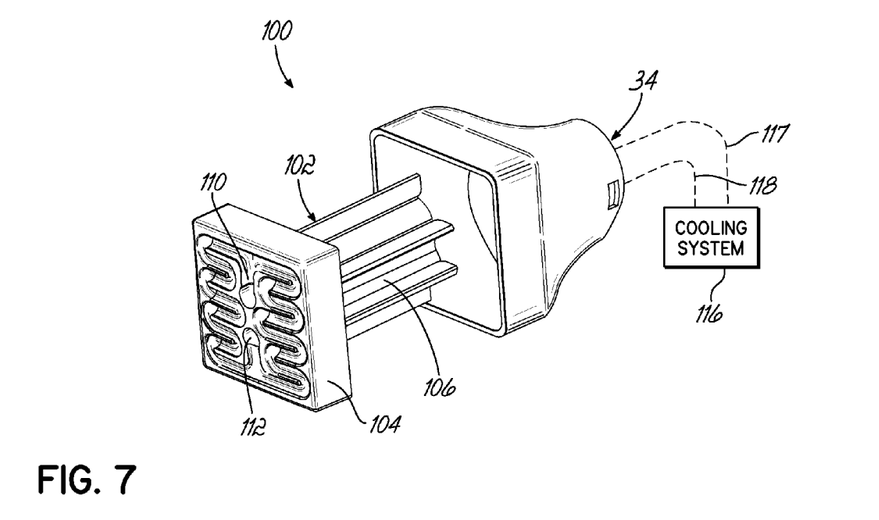
FIG. 7 is an exploded front view of an alternative embodiment of an electrode structure for use with the treatment tip of FIGS. 2, 2A, and 3.

Coolants other than coolant sprays are contemplated by the invention. The invention contemplates and includes any means and method for cooling skin and epidermis. So, for example, if a heat transfer body 35 is used to cool a back surface of the electrodes and metal sections 602, this body could be cooled with a thermoelectric cooler (FIG. 8) or a closed loop fluid cooling circuit (FIG. 7). In addition, though desired, a heat transfer body is not required by the invention. Rather, a back surface of the electrodes 60, 62, 64, 66 and metal sections 602 could be directly cooled with a thermoelectric cooler, a closed loop fluid cooling circuit, or by a coolant spray.

Single electrode treatment tips are limited in surface area because of the load imposed on a high frequency power supply scales with the surface area. Consequently, for example, a high frequency power supply may have a maximum power output, say about 400 watts. For a specific electrode construction, this maximum power output will only be sufficient to energize an electrode of a given size, say about 3 $cm^2$. Consequently, according to an embodiment of the invention, multiple electrodes of about 3 $cm^2$ each can be formed in an array. For the example described, four such electrodes can be used making the array size 12 $cm^2$. If isolated metal sections are disposed between and around the individual electrodes, the total size of the array can be on the order of about 15 $cm^2$ or about 16 $cm^2$. So for a given high frequency power supply, the effective surface area of the electrode array can be significantly increased, while not having a corresponding increase in treatment time since cooling and energy delivery can occur in parallel, and a treating clinician spends less time moving an electrode from place to place on a patient's skin. Compared with a single electrode treatment tip of smaller size, the multi-electrode treatment tip 14 permits gains in treatment efficiency because the existence of multiple electrodes, each of which may be comparable in surface area to the one electrode of a single electrode treatment tip, can be sequentially energized to deliver high frequency energy to different regions of tissue without moving the treatment tip 14.

In a preferred embodiment, four such electrodes 60, 62, 64, 66 are here described in relation to treatment tip 14. However, in alternative embodiments, any larger or smaller number of electrodes may be chosen. The electrodes 60, 62, 64, 66 can be sized such that a maximum power to energize any single electrode is approximately equal to the maximum power output of the high frequency power supply 20. In this example, the maximum power to energize any two of the electrodes 60, 62, 64, 66 would exceed the maximum power output of the high frequency power supply 20. According to an alternative embodiment, the electrodes 60, 62, 64, 66 may be made smaller in size, and groups of the electrodes 60, 62, 64, 66 may be sequentially powered, with the power required to energize any single group being slightly less than the maximum output power of the power supply 20.

In various embodiments, each of the electrodes 60, 62, 64, 66 may have a surface area greater than about 1 cm$^2$ and, in particular, each of the electrodes 60, 62, 64, 66 may have a surface area in the range of about 1 cm$^2$ to about 20 cm$^2$. In specific embodiments, each of the electrodes 60, 62, 64, 66 may have a surface area of about 1 cm$^2$, about 1.5 cm$^2$, about 3 cm$^2$, about 5 cm$^2$, about 7 cm$^2$, about 10 cm$^2$, about 15 cm$^2$, or about 20 cm$^2$.

Lasers have been utilized in conjunction with cosmetic surgical techniques for delivering a pattern of discrete microscopic thermal wounds to the skin and underlying tissue. However, the cross-sectional area of each thermal wound evaluated in a direction perpendicular or normal to the skin surface is on the order of a square micron in size. In contrast, the corresponding treated cross-sectional area of tissue for each of the electrodes 60, 62, 64, 66 is approximately equal to the electrode surface area and, therefore, is significantly larger by several orders of magnitude than the cross-sectional area of thermal wounds created by lasers.

Figure 2:
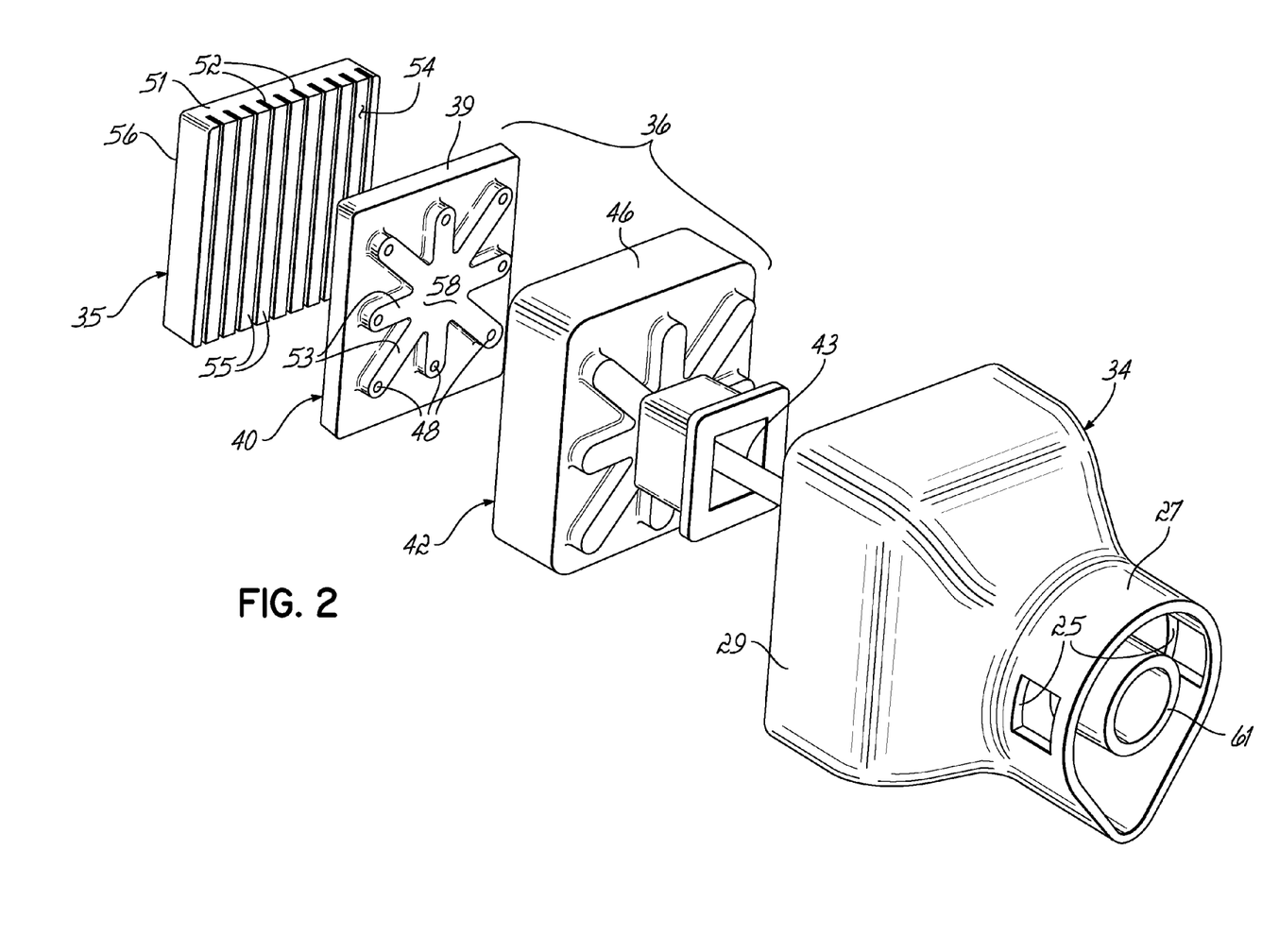
FIG. 2 is an exploded rear view of a portion of the treatment tip of FIG. 1 with the energy delivery member omitted for clarity of illustration.
Figure 2A:
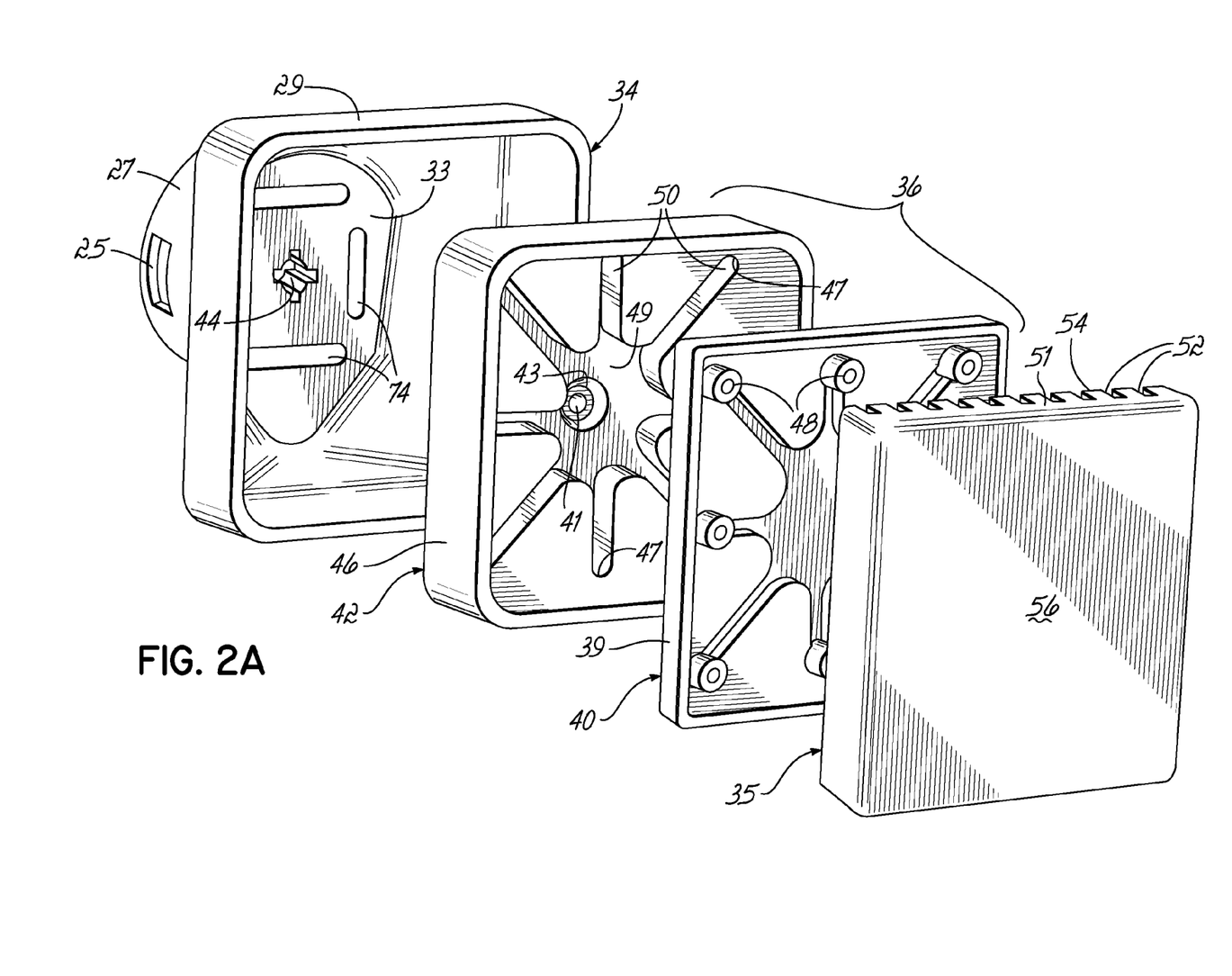
FIG. 2A is an exploded front view of the portion of the treatment tip shown in FIG. 2 with the energy delivery member omitted for clarity of illustration.
Figure 3:
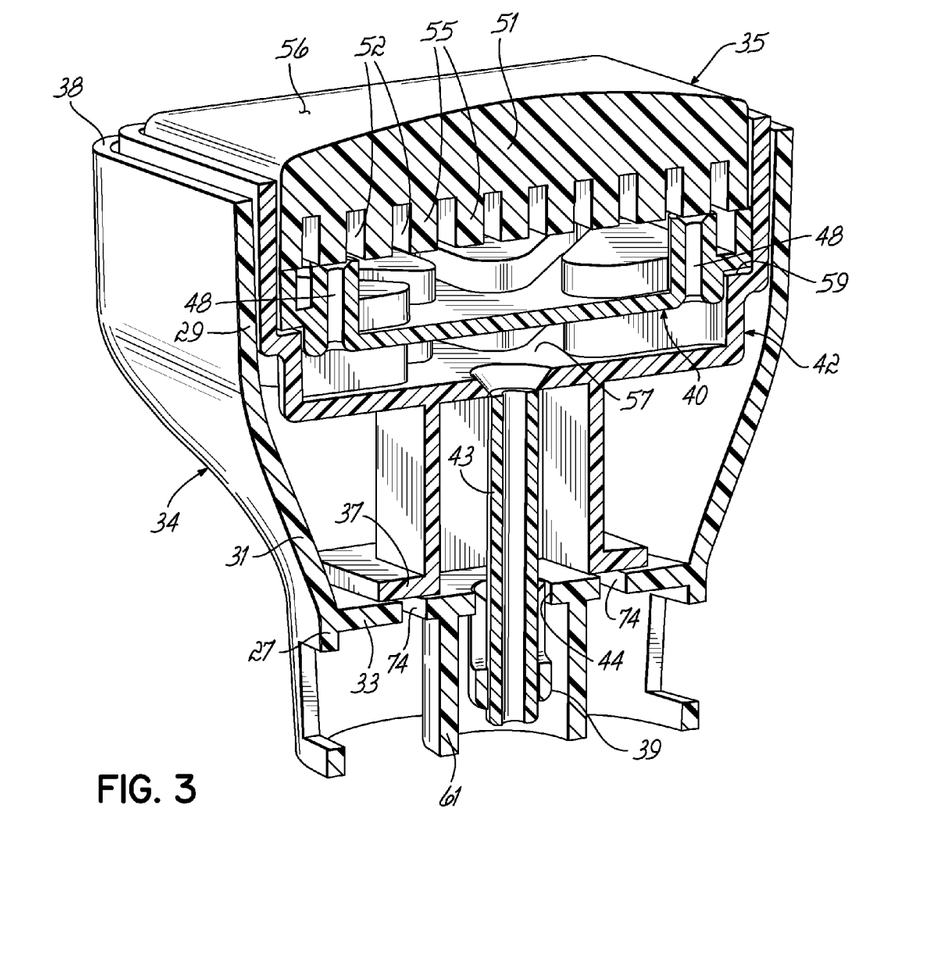
FIG. 3 is a cross-sectional view taken generally along line 3-3 in FIG. 1 with the energy delivery member removed for clarity of illustration.

With reference to FIG. 7 in which like reference numerals refer to like features in FIGS. 1-6 and in accordance with an alternative embodiment of the invention, a treatment tip 100 includes a fluid delivery member 102 that replaces heat transfer body 35 and fluid delivery member 36 (FIGS. 2, 2A). In addition to the fluid delivery member 102, the treatment tip 100 includes the outer shell 34. The insulating substrate 68 of the energy delivery member 16 is wrapped or folded about the fluid delivery member 102, as best shown in FIG. 4A and as understood by a person having ordinary skill in the art.

The fluid delivery member 102 includes a front section 104, a stem 106 projecting rearwardly from the front section 108, and ribs projecting from the stem 106 that are used to position the fluid delivery member 102 inside the outer shell 34. The dimensions of the outer shell 34 may be adjusted to accommodate the fluid delivery member 102. The front section 104 of the fluid delivery member 102 includes a channel 110 that, in the assembly constituting treatment tip 100, underlies the electrodes 60, 62, 64, 66. The insulating substrate 68 of the energy delivery member 16 may be bonded with a rim of the front section 104 to provide a fluid seal that confines coolant flowing in the channel 110. Channel 110 includes convolutions that are configured to optimize the residence time of the coolant in channel 110, which may in turn optimize the heat transfer between the coolant and the electrodes 60, 62, 64, 66.

An inlet bore or passage 112 and an outlet bore or passage 114 extend through the stem 106 of the fluid delivery member 102. The inlet passage 112 and outlet passage 114 are rearwardly accessible through the outer shell 34. The channel 110 is bifurcated into two channel sections so that fluid flow in the channel 110 diverges away in two separate streams from the inlet passage 112 and converges together to flow into the outlet passage 114. Fluid pressure causes the coolant to flow from the inlet passage 112 through the two channel sections to the outlet passage 114. The circulating coolant, which may be water or another fluid, directly contacts a rear surface of the energy delivery member 16.

Fluid connections are established with the inlet passage 112 and outlet passage 114 in the stem 106 of the fluid delivery member 102 to establish a closed circulation loop with a cooling system 116. The closed circulation loop permits a re-circulating coolant flow to and from the channel 110 in the fluid delivery member 102 when the treatment tip 100 is mated with the handpiece 12. A delivery line 117 supplies a stream of the coolant from the cooling system 116 to the inlet passage 112. A return line 118 returns the coolant from the outlet passage 114, which is warmed after absorbing the heat energy, back to the cooling system 116 to complete the closed circulation loop. The cooling system 116 includes a reservoir holding a volume of a coolant, a pump that continuously pumps a stream of the coolant from the reservoir to the inlet passage 112, and a cooling device configured to maintain the temperature of the coolant held within the reservoir at a desired temperature.

Figure 8:
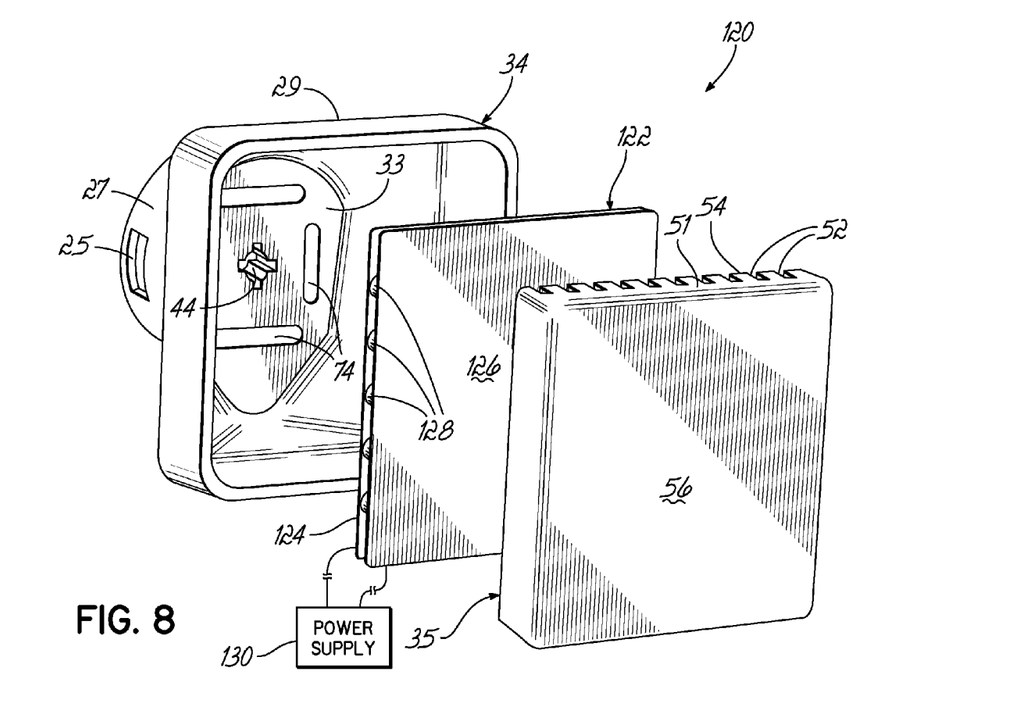
FIG. 8 is an exploded front view of an alternative embodiment of an electrode structure for use with the treatment tip of FIGS. 2, 2A, and 3.

With reference to FIG. 8 in which like reference numerals refer to like features in FIGS. 1-6 and in accordance with an alternative embodiment of the invention, a treatment tip 120 includes a thermoelectric cooler 122 that replaces fluid delivery member 36 (FIGS. 2, 2A). The thermoelectric cooler 122 includes a first support plate 124, a second support plate 126 that is in thermal contact with the heat transfer body 35, and multiple thermoelectric elements 128 extending between the first and second support plates 124, 126. The thermoelectric elements 128 consist of an array of up to several hundred dissimilar n-type and p-type semiconductors thermally joined in parallel and electrically joined in series at both ends to form couples. The first and second support plates 124, 126 may be thin ceramic wafers with a relatively high thermal conductivity that add rigidity to the thermoelectric cooler 122 and electrically insulate the thermoelectric elements 128. One or both of the support plates 124, 126 includes a circuit interface used to electrically couple the thermoelectric elements 128 with the terminals of a power supply 130.

The thermoelectric cooler 122 operates by the Peltier effect, as understood by a person having ordinary skill in the art, to convert electrical energy delivered from the power supply 130 to heat pumping energy used to cool the heat transfer body 35. In particular, direct current power applied between the first and second support plates 124, 126 induces pumped heat flow from the heat transfer body 35 through the thermoelectric elements 128 to the outer shell 34 as the thermoelectric element 128 converts electrical energy to heat pumping energy. Heat is conducted through the thermoelectric elements 128 and between the support plates 124, 126 by charge carriers. Heat is continuously absorbed by the second support plate 126 and transferred by the thermoelectric elements 128 to the first support plate 124. The second support plate 126 defines a cold side of the thermoelectric cooler 122 that absorbs heat from the heater transfer body 35 and the first support plate 124 defines a hot side that rejects the heat. The outer shell 34 and handpiece 12 are configured to operate as a heat sink that is in thermal contact with the first support plate 124 and that receives the heat rejected by the first support plate 124 of the thermoelectric cooler 122.

In an alternative embodiment, the heater transfer body 35 may be omitted from the treatment tip 120 so that the second support plate 126 of the thermoelectric cooler 122 is in direct contact with a confronting rear surface of the energy delivery member 16.

Figure 9:
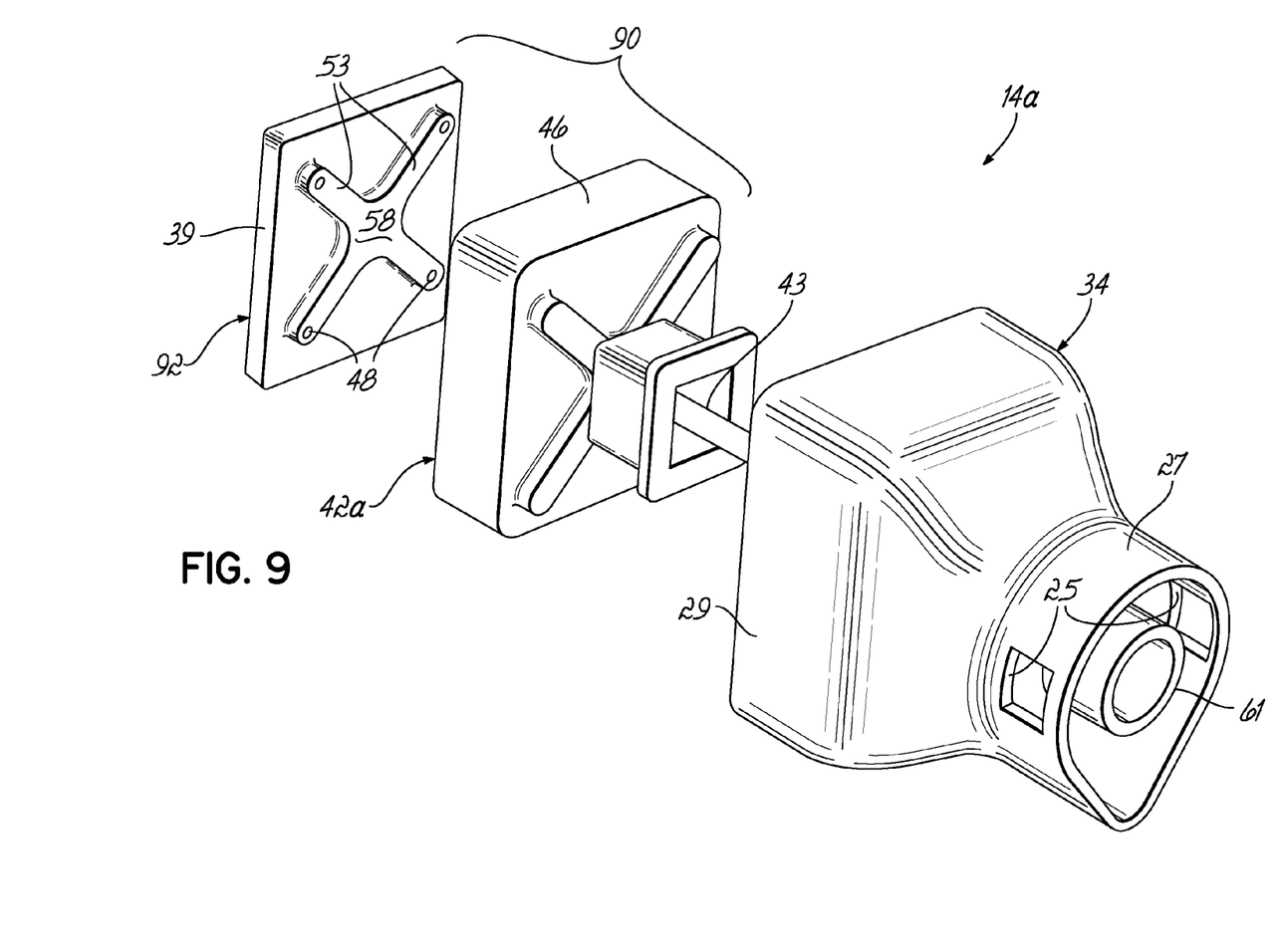
FIG. 9 is an exploded rear view similar to FIG. 2 of a portion of a treatment tip in accordance with an alternative embodiment of the invention.
Figure 9A:
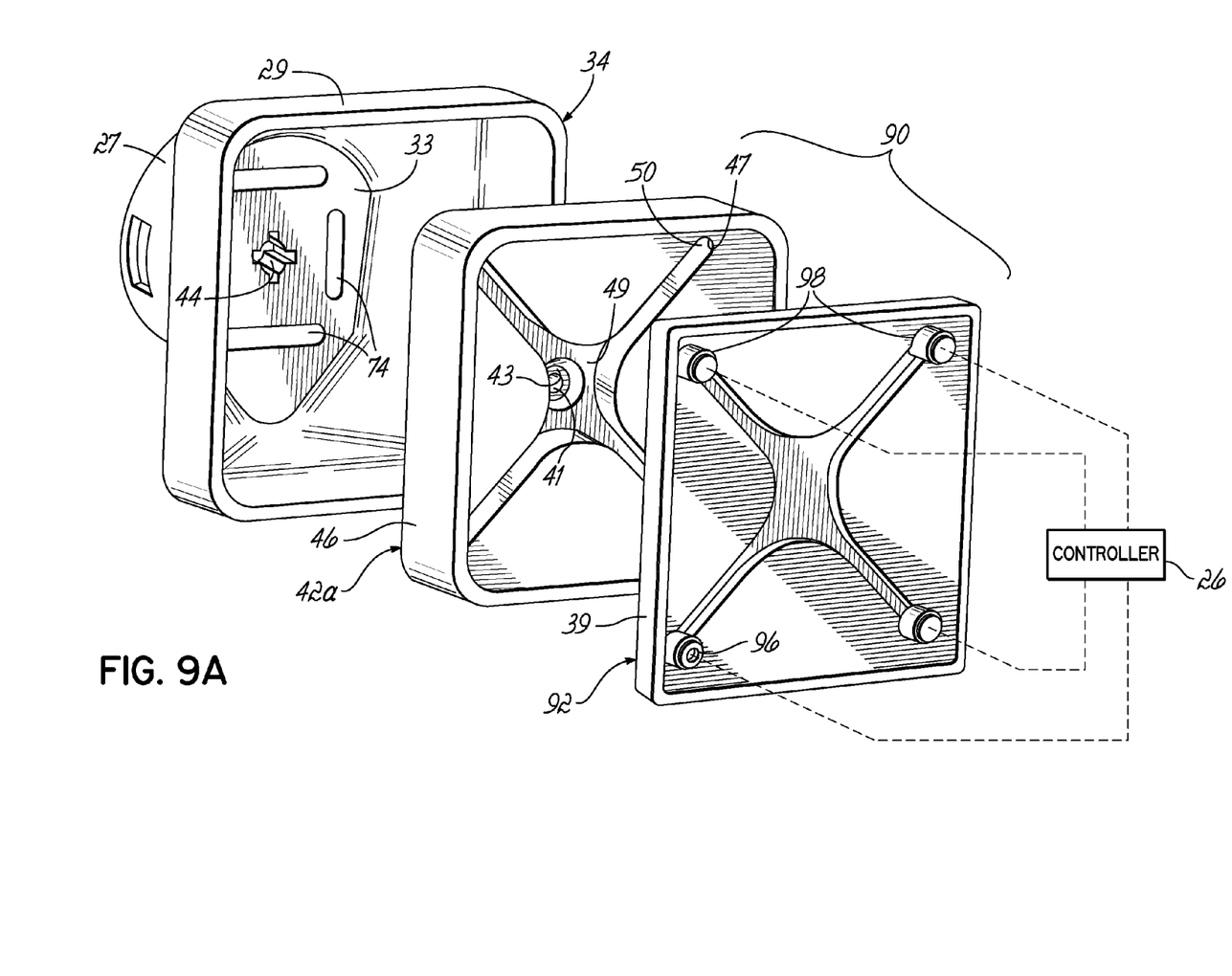
FIG. 9A is an exploded front view of the portion of the treatment tip shown in FIG. 9.

With reference to FIGS. 9 and 9A in which like reference numerals refer to like features in FIGS. 1-6 and in accordance with an alternative embodiment of the invention, a treatment tip 14a includes a fluid delivery member 90 with a fluid coupling member 92 that replaces the fluid coupling member 40 (FIGS. 2, 2A). Fluid coupling member 92 is coupled with fluid coupling member 42 to constitute the fluid delivery member 90, as described with regard to fluid coupling member 40. The heat transfer body 35 (FIGS. 2, 2A) is omitted from the construction of treatment tip 14a.

Fluid coupling member 92 includes the passages 48 each having an outlet 96 from which a spray of coolant is discharged. Associated with each of the passages 48 is a valve 98 that individually regulates the coolant discharge. In the assembled treatment tip 14, the outlet 96 of each of the passages 48 is oriented to direct the discharged coolant toward the insulating substrate 68 at a location correlated with one of the electrodes 60, 62, 64, 66. The fluid coupling member 42a includes fewer channels 50 but is otherwise identical to fluid coupling member 42 (FIGS. 1-6).

In use and with reference to FIGS. 6, 9, and 9A, the coolant is supplied from the fluid coupling member 40 to the fluid delivery member 90 and discharged from the outlet 96 of one of the passages 48 to impinge electrode 60. A first region of the patient's tissue near electrode 60 is thereafter pre-cooled by heat transfer through the energy delivery member 16 of treatment tip 14. Switch 82 of the switching element 80 is used to close the current path between electrode 60 of the energy delivery member 16 and power supply 20. After a brief interval to permit a depth of the tissue in the first region to cool to a targeted temperature, electrode 60 is energized by power supply 20 to deliver high frequency energy to the first tissue region over a first time period. Switches 84, 86, 88 remain open so that electrodes 62, 64, 66 are unpowered.

While electrode 60 is energized over the first time period, another of the passages 48 can be used to discharge coolant to impinge the insulating substrate 68 underlying electrode 62 for pre-cooling a second region of the patient's tissue near electrode 62. Alternatively, the pre-cooling may occur after the electrode 60 is de-energized. However, the ability to individually rely on the valves 98 to control coolant discharge permits the simultaneous delivery over the first time period of high frequency energy from electrode 60 while pre-cooling in the vicinity of electrode 62 or any other combination of electrodes.

After switch 82 of switching element 80 opens the current path to electrode 60, switch 84 of the switching element 80 is closed to form a closed circuit with a signal or current path defined between electrode 62 of the energy delivery member 16 and the power supply 20. While high frequency energy is delivered from electrode 62 to the precooled second region of the tissue over a second time period, yet another of the passages 48 can be used to discharge coolant by opening another of the valves 98 to impinge the insulating substrate 68 underlying electrode 64 to pre-cool a third region of the patient's tissue near electrode 64. Switches 86 and 88 remain open during the second time period. Simultaneously and optionally, the first treated region of the patient's tissue underlying electrode 60 can be post-cooled by opening the associated valve 98 and permitting another discharge of coolant from the outlet 96 of the passage 48 aimed at the insulating substrate 68 underlying electrode 60.

This process is reiterated for two additional time periods that energize electrodes 64, 66. At the conclusion of the treatment process, each of the electrodes 60, 62, 64, 66 has been serially pre-cooled, energized, and post-cooled to treat a corresponding plurality of tissue regions. Therefore, the treatment tip 14a is moved to a different treatment site on the patient's skin surface and the sequence for energizing and cooling the electrodes 60, 62, 64, 66 is repeated.

As a result of the ability to individually cool each of the electrodes 60, 62, 64, 66, high frequency energy can be delivered across the entire surface area of the energy delivery member 16 without moving the treatment tip 14a. The tissue regions are treated while limiting the load on the power supply 20 and, therefore, while limiting the load on the main power presented by the power supply 20. Scaling the surface area of the electrodes 60, 62, 64, 66 determines the treatment area for each treatment site. The ability to concurrently pre-cool one or more of the electrodes 60, 62, 64, 66 and optionally post-cool another one or more of the electrodes 60, 62, 64, 66, while simultaneously delivering high frequency energy from yet a different one or more of the electrodes 60, 62, 64, 66, improves the time-efficiency for using treatment tip 14a.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method of operating a tissue treatment apparatus for treating tissue located beneath a skin surface with high frequency energy from a plurality of electrodes that are electrically isolated from each other, the method comprising:
    cooling a first electrode to cool a first region of the tissue by heat transfer through the first electrode;
    delivering the high frequency energy from the first electrode over a first time period to treat the cooled first region of the tissue;
    cooling a second electrode during the first time period to cool a second region of the tissue by heat transfer through the second electrode;
    delivering the high frequency energy from the second electrode, while cooled, over a second time period subsequent to the first time period; and
    after the high frequency energy is delivered from the first electrode, cooling the first electrode during the second time period to cool the treated first region of the tissue by heat transfer through the first electrode.

2. The method of claim 1 wherein cooling the first electrode further comprises:
    delivering a coolant from a first nozzle with a passage oriented to discharge the coolant at the first electrode.

3. The method of claim 1 further comprising:
    cooling a third electrode during the second time period to cool a third region of the tissue by heat transfer through the third electrode.

4. The method of claim 3 further comprising:
    uncoupling the first electrode from a source of the high frequency energy after the first time period concludes.

5. The method of claim 4 further comprising:
    coupling the second electrode with the source of the high frequency energy after the first time period concludes.

6. A method of operating a tissue treatment apparatus for treating tissue located beneath a skin surface with high frequency energy from a plurality of electrodes that are electrically isolated from each other, the method comprising:

delivering the high frequency energy from a first electrode over a first time period to treat a first region of the tissue;

delivering the high frequency energy from a second electrode over a second time period, after the conclusion of the first time period, to treat a second region of the tissue; and cooling the second electrode during the first time period to cool the second region of tissue by heat transfer through the second electrode.

7. The method of claim 6 further comprising:

cooling the first electrode to cool the first region of the tissue, before the first time period begins, by heat transfer through the first electrode.

8. The method of claim 6 further comprising:

cooling the first electrode during the second time period to cool the first region of the tissue after the high frequency energy is delivered.

9. The method of claim 7 wherein cooling the first electrode further comprises:

cooling the first electrode after the first time period concludes to cool the first region of the tissue by heat transfer through the first electrode.

10. The method of claim 6 wherein cooling the second electrode further comprises:

cooling the second electrode before the second time period begins to cool the second region of tissue by heat transfer through the second electrode.

11. The method of claim 6 wherein high frequency energy is not delivered from the first electrode to the first region of the tissue over the second time period.

12. The method of claim 1 wherein the first and second electrodes are disposed between a source of the cooling and the first and second regions of the tissue.

13. The method of claim 6 wherein the first and second electrodes are disposed between a source of the cooling and the first and second regions of the tissue.

14. The method of claim 1 wherein the high frequency energy delivered from the first and second electrodes provides a non-invasive tissue treatment.

15. The method of claim 6 wherein the high frequency energy delivered from the first and second electrodes provides a non-invasive tissue treatment.

16. The method of claim 1 wherein the high frequency energy delivered from the first and second electrodes provides a non-ablative tissue treatment.

17. The method of claim 6 wherein the high frequency energy delivered from the first and second electrodes provides a non-ablative tissue treatment.

18. The method of claim 1 wherein the tissue is skin tissue, and the high frequency energy is delivered through the skin surface to the skin tissue.

19. The method of claim 6 wherein the tissue is skin tissue, and the high frequency energy is delivered through the skin surface to the skin tissue.

\* \* \* \* \*